United States Patent
Chen et al.

(10) Patent No.: US 7,256,894 B2
(45) Date of Patent: Aug. 14, 2007

(54) METHOD AND APPARATUS FOR PERFORMING SECOND HARMONIC OPTICAL COHERENCE TOMOGRAPHY

(75) Inventors: Zhongping Chen, Irvine, CA (US); Yi Jang, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 333 days.

(21) Appl. No.: 10/970,485

(22) Filed: Oct. 20, 2004

(65) Prior Publication Data

US 2005/0140982 A1 Jun. 30, 2005

Related U.S. Application Data

(60) Provisional application No. 60/512,675, filed on Oct. 20, 2003.

(51) Int. Cl.
*G01B 9/02* (2006.01)
(52) U.S. Cl. .................................... 356/497; 356/489
(58) Field of Classification Search ................ 356/479, 356/497, 489, 486, 485
See application file for complete search history.

(56) References Cited

U.S. PATENT DOCUMENTS 6,608,717 B1 * 8/2003 Medford et al. ............ 359/368
6,611,339 B1 * 8/2003 Yang et al. ................. 356/485

* cited by examiner

*Primary Examiner*—Hwa (Andrew) Lee
(74) *Attorney, Agent, or Firm*—Myers Dawes Andras & Sherman LLP

(57) ABSTRACT

The invention is an apparatus and method for second harmonic optical coherence tomography of a sample comprising a laser coupled to an interferometer which has a reference arm and in a sample arm. A nonlinear crystal in the reference arm generates a second harmonic reference signal. The sample typically backscatters some second harmonic light into the sample arm. A broadband beam splitter optically coupled to the reference arm and sample arm combines the signals from the reference arm and sample arm into interference fringes and a dichroic beam splitter splits the interference fringes into a fundamental and second harmonic interference signal. A detector is optically coupled to the dichroic beam splitter detects interference fringes from which both an OCT and second harmonic OCT image can be constructed using a conventional data processor.

52 Claims, 10 Drawing Sheets

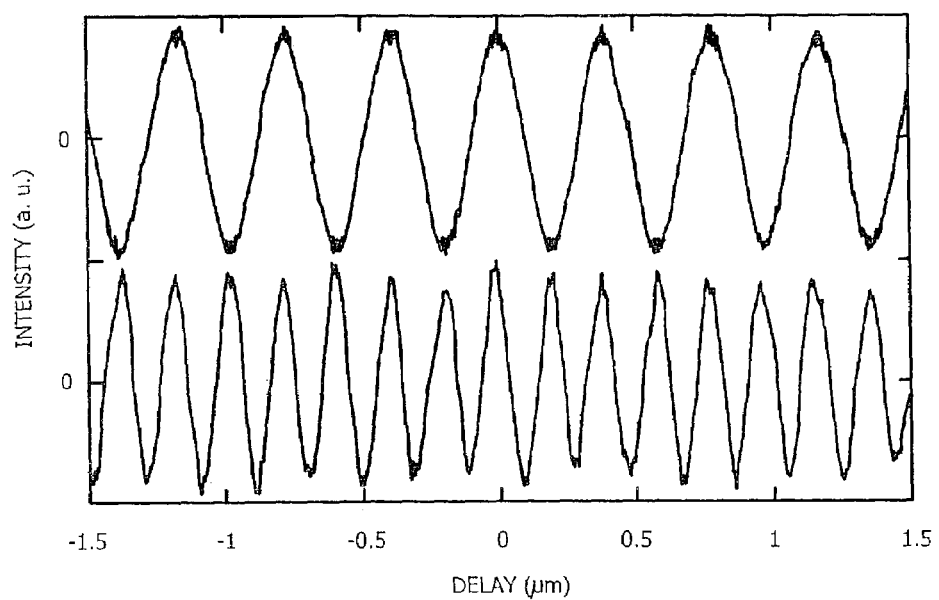
FIG. 2
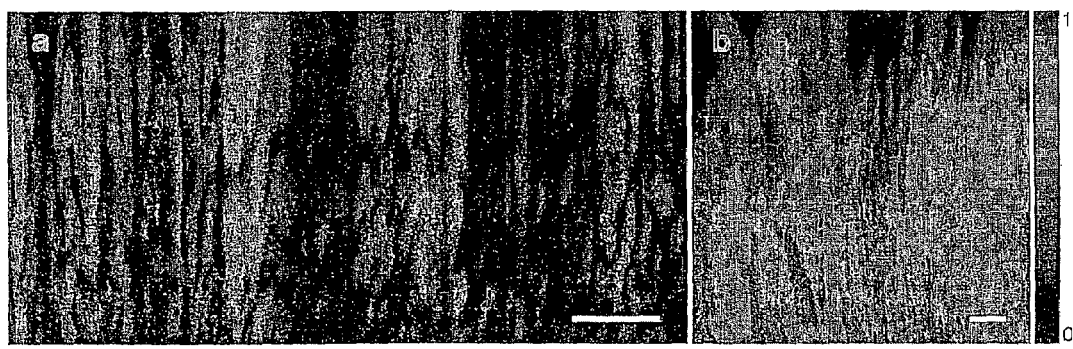
FIG. 6A
FIG. 6B

METHOD AND APPARATUS FOR PERFORMING SECOND HARMONIC OPTICAL COHERENCE TOMOGRAPHY

RELATED APPLICATIONS

The present application is related to U.S. Provisional Patent Application, Ser. No. 60/512,675, filed on Oct. 20, 2003, which is incorporated herein by reference and to which priority is claimed pursuant to 35 USC 119.

BACKGROUND OF THE INVENTION

1. Field of the Invention

The invention relates to the field of optical coherence tomography using optical second harmonic generation and nonlinear optical interferometry.

2. Description of the Prior Art

Optical coherence tomography (OCT) is an emerging imaging technology that provides in-vivo high-resolution, cross-sectional images of biological tissues. Using coherence gating technique, OCT is capable of detecting the backscattered light from highly scattering tissues at depths of 2-3 mm. OCT imaging contrast originates from the inhomogeneities of sample scattering properties that are linearly dependent on sample refractive indices. In many instances such as pathological processes in tissue, changes in sample linear scattering properties are small and difficult to measure. For example, many cancers originate in the epithelium that has a thickness suitable for OCT imaging, but in their early stages when these cancers are developing through cell dysplasia, changes in tissue morphology and refractive index between normal and diseased tissues are very small and difficult to detect. Therefore, to meet the challenges found in OCT clinical applications, imaging contrast enhancement is very important.

In recent years, many OCT contrast enhancement methods have been developed. These techniques include Doppler OCT, polarization sensitive OCT, spectroscopic OCT, pump-probe techniques, and using contrast agents for OCT. More recently, applying nonlinear optical effects of second harmonic generation (SHG) and coherent anti-Stokes Raman scattering for OCT contrast enhancement have also been demonstrated.

SHG is a powerful contrast mechanism in nonlinear optical microscopy. SHG signals provide unique information regarding sample structure symmetry because the signals strongly depend on the orientation, polarization and local symmetry properties of chiral molecules. SHG enables direct imaging of anisotropic biological structures, such as membranes, structure proteins, and microtubule ensembles. Besides successfully producing high-resolution and highly contrasting images of tissue morphology, recently SHG microscopy has also been applied to study dynamics in tissue physiology, such as monitoring collagen modification in tumors growing, and optically recording the action potentials change in neuron cells. SHG is emerging as a powerful nonlinear optical imaging modality for cell biology and biophysics.

BRIEF SUMMARY OF THE INVENTION

In the illustrated embodiment the invention is defined as an apparatus for second harmonic optical coherence tomography of a sample comprising a light source, such as a femtosecond pulsed laser, and an interferometer having an optical path in a reference arm and in a sample arm. A nonlinear crystal is disposed in the optical path of the reference arm. The sample in the optical path of the sample arm backscatters at least some second harmonic of the incident light. A broadband beam splitter is optically coupled to the reference arm and sample arm, combines the signals in the reference arm and sample arm into interference fringes. A dichroic beam splitter is optically coupled to the broadband beam splitter to splits the interference fringes into a fundamental and second harmonic interference signal. A detector is optically coupled to the dichroic beam splitter for detecting interference fringes, which include at least the second harmonic interference fringes, and a second detector preferably detects the fundamental harmonic interference fringes. The interferometer and detector simultaneously perform second harmonic OCT measurements at second harmonic frequency and conventional OCT measurements at a fundamental frequency.

A pair of prisms is disposed in the optical path of the signal arm or reference arm to compensate for the group-velocity dispersion of the fundamental and harmonic waves or group velocity mismatch in the signal arm and reference arm, thus enabling simultaneous observation of SH-OCT interference signals and conventional OCT interference signals.

The interferometer comprises means for independently axially or transversely scanning the sample in decoupled modes of operation to provide two dimensional tomographic imaging of the sample with only one dimensional movement of the light.

The apparatus further comprises optical elements, such as half wave plates and laser polarizers, for controlling input power into the interferometer.

In the embodiment where the light source comprises a mode-locked laser the apparatus further comprises an optical isolator for preventing back-scattered light from entering the light source and interfering with mode locking.

The apparatus further comprises optical elements, such as filters for filtering out second harmonic frequencies of light generated by the light source.

The apparatus further comprises optical elements coupled to the light source for determining a ratio of polarization modes of the light generated by the light source and for splitting the light from the light source into the reference arm and sample arm according to polarization mode of the light.

In the illustrated embodiment the nonlinear crystal is oriented for type I phase matching.

A dichroic mirror and translation stage coupled to the mirror serve as an optical terminus in the reference arm to act as an optical delay line. The dichroic mirror differentially reflects the fundamental and second harmonic frequency of the light signal in the reference arm to reduce the amount of reflected light at the fundamental frequency, which is transmitted toward the nonlinear crystal.

A bandpass filter centered at the second harmonic frequency and optically coupled to the dichroic beam splitter rejects background noise transmitted toward the detector.

A long pass filter and short pass filter differentiate between the fundamental and second harmonic frequency interference signals. The first detector which detects the fundamental frequency is optically filtered by the long pass filter and the second detector which detects the second harmonic frequency is optically filtered by the short pass filter.

A moving mirror is disposed in the reference arm and a lock-in amplifier is coupled to the detector. The lock-in amplifier is locked at $f_{1,2}=2v\,\Delta l/\lambda_{1,2}$, where $v$ and $\Delta l$ are the frequency and amplitude respectively of the moving mirror, and $\lambda_{1,2}$ are the wavelengths of the fundamental and second harmonic interference signals.

Additional optical elements can be disposed into the interferometer optical path for controlling the beam polarization of light in the sample arm and reference arm, oriented according to polarization characteristics of the sample.

The nonlinear crystal has a predetermined thickness according to the wavelength of the fundamental frequency for balanced SHG signal strength and spectral width. The predetermined thickness is approximately 0.1 mm when the wavelength of the fundamental frequency is approximately 800 nm.

The invention is also defined as a method of operating the forgoing apparatus to generate second harmonic OCT images and conventional OCT images. For example, the invention includes a method of performing optical tomography of a sample comprising the steps of providing a source of at least partially coherent broadband radiation through an interferometer having a sample arm for probing the sample and a reference arm; scanning the sample with the source of radiation through the interferometer; generating first and second harmonics from the sample and from a nonlinear thin crystal in the reference arm; detecting interference fringes of the first and second harmonics radiation backscattered from the sample into the interferometer; processing the detected interference fringes to determine first and second harmonics OCT signals of the detected backscattered interference fringes at each pixel in a data window; and generating a tomographic image of the sample at each pixel based on the first and second harmonics OCT interference fringes. In the same manner, the invention is an apparatus for performing optical tomography of a sample in which second harmonics of a radiation signal can be generated according to the above method.

The invention can be further defined as an improvement in an OCT tomographic imaging system having an interferometer with a reference arm and sample arm comprising means for generating a second harmonic frequency in the reference arm; means for combining the second harmonic frequency from the reference arm and a second harmonic frequency from the sample in the sample arm to produce a second harmonic interference fringe signal; and means for detecting the second harmonic interference fringe signal to enable the OCT tomographic imaging system to produce an image derived from the second harmonic interference fringe signal. Again, the invention can be defined as an improvement in a method of OCT tomographic imaging using an interferometer with a reference arm and sample arm in the foregoing improved system.

The invention can be further defined as an improvement in an OCT tomographic imaging system comprising means for generating third harmonic frequency in the reference arm, by replacing the nonlinear crystal with one optimized for third harmonic generation; means for combining the third harmonic frequency from a nonlinear crystal in the reference arm and a third harmonic frequency from the sample in the sample arm to produce a third harmonic interference fringe signal; and means for detecting the third harmonic interference fringe signal to enable the OCT tomographic imaging system to produce an image derived from the third harmonic interference fringe signal.

The invention can be further defined as an improvement in an OCT tomographic imaging system comprising means for generating a Raman frequency in the reference arm, by replacing the nonlinear crystal with a Raman reference; means for combining the Raman frequency from the Raman reference in the reference arm and a Raman frequency from the sample in the sample arm to produce a Raman interference fringe signal; and means for detecting the Raman interference fringe signal to enable the OCT tomographic imaging system to produce an image derived from the Raman interference fringe signal. The Raman reference may be any known sample or material which is capable of producing a known Raman frequency, typically in the range close to that expected in the unkown or imaged sample.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 2 are graphs of the fundamental and second harmonic interference signals respectively as function of delay in μm in the interferometer of FIG. 1a. The second harmonic interference signal is at double the frequency of the fundamental harmonic interference signal.

FIGS. 3a-3d are graphs of coherence length measurements of the hybrid OCT system of FIG. 1a. FIG. 3a is the emission spectrum of intensity verses wavelength of a pump laser with a spectral width of 8.1 nm. FIG. 3b is the spectrum of intensity of the second harmonic wave from a BBO crystal with a spectral width of 3.0 nm. FIG. 3c is the spectrum of intensity of measured interference fringes at the fundamental wavelength showing a free-space axial resolution of 33 μm for conventional OCT. FIG. 3d is the spectrum of intensity of measured interference fringes at the second harmonic wavelength showing a free-space axial resolution of 24 μm for second harmonic OCT.

FIG. 4a shows the consecutive reflection interfaces of the phantom while FIG. 4b only highlights the collagen layers.

FIG. 5a is a graph of the spectrum of the fundamental wave. The narrow curve is the original spectrum of the laser, and the broader curve is the spectrum of the continuum generated from the fiber. FIG. 5b is a graph of the spectrum of the second harmonic wave from the nonlinear crystal in the apparatus. FIG. 5c is a coherence point spread function of the fundamental wave with the coherence length measured to be 6.0 μm. FIG. 5d is a coherence point spread function of the second harmonic wave, with the coherence length measured to be 4.2 μm.

FIG. 6a is an SH-OCT image showing an area of 100×50 μm in the rat-tail tendon, where many cable-like, parallel oriented, and slightly wavy collagen fiber bundles (fascicles) can be clearly seen. FIG. 6b is a 60× microscope image of the same sample. The scale bar is 10 μm in length.

Figure 1A:
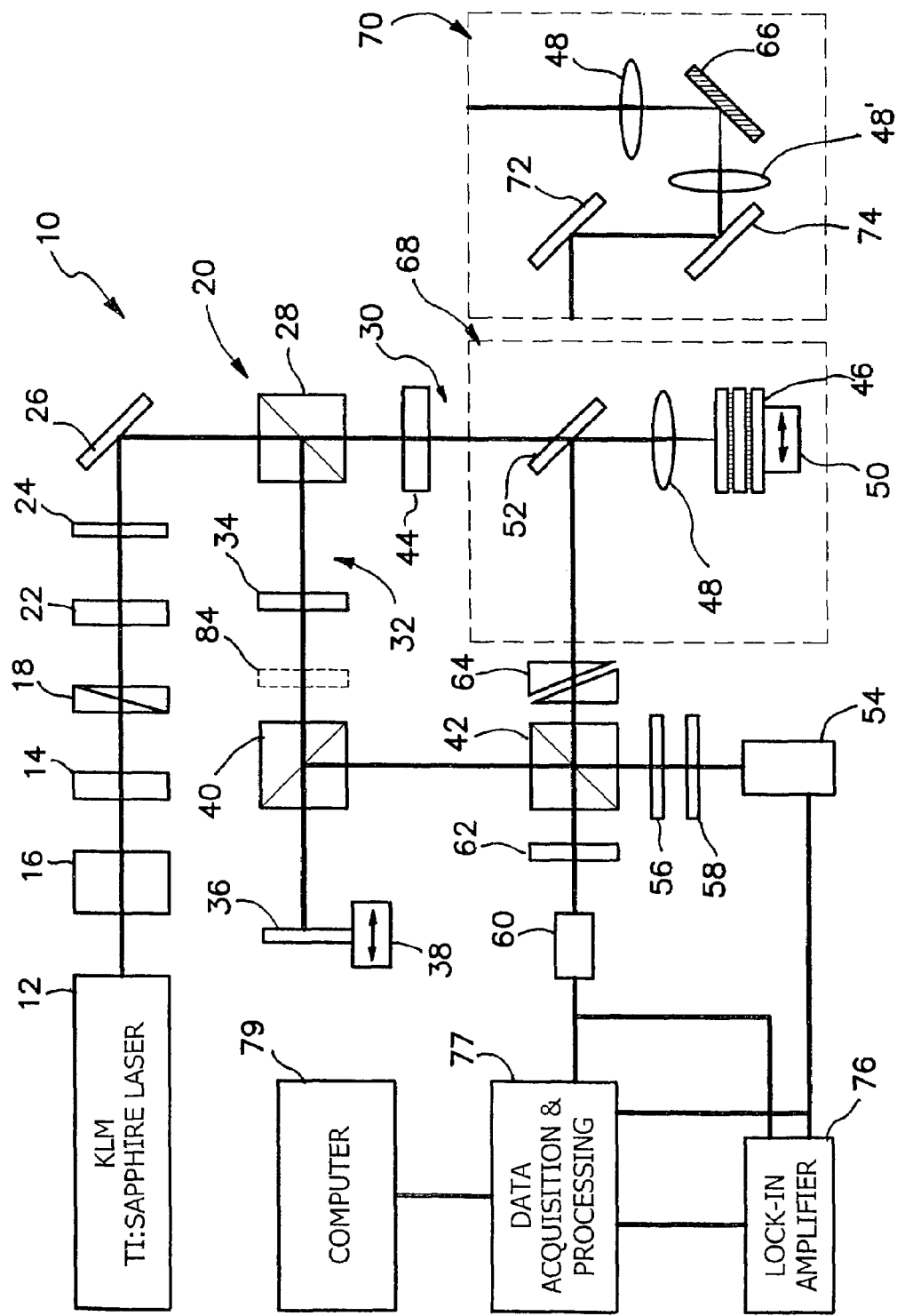
FIG. 1a is a schematic diagram of a second harmonic OCT apparatus, which is implemented in a free-space Mach-Zehnder interferometer configuration.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

An optical tomography technique of second harmonic optical coherence tomography is described. Femtosecond laser pulses at 800 nm wavelength are used to excite second harmonics at 400 nm from a rat tail tendon and a reference nonlinear thin crystal 34. Second harmonic interference fringe signals were detected and used for image construction. A tomographic image shows the sample structure of two thin collagen layers sandwiched among glass slides as shown and described below in connection with FIG. 4c. Because of the strong dependence of second harmonic generation on molecular and tissue structures, this technique offers molecular contrast as well as resolution enhancement to the conventional optical coherence tomography.

The invention discloses a high-resolution SH-OCT system 10 as diagrammatically described below in FIG. 1b. Using broadband, pulsed laser illumination and nonlinear interferometry, the system 10 combines the molecular structure sensitivity of SHG with coherence gating of OCT. Since the axial and transverse scans are decoupled, two-dimensional cross-sectional imaging of anisotropic biological structures can be done with one-dimensional scanning of the sampling beam, which has the potential to be adapted to clinic endoscopic studies.

In the illustrated embodiment, a high numerical aperture single mode fiber 17 is used to broaden the spectrum of a femtosecond laser 12. The sample 46 under illumination generates second harmonic generated (SHG) signal. The reference SHG signal is generated by a nonlinear crystal 34. Coherence gating detection of these SHG signals produces interference fringes that can be used for image construction. The current system achieves an axial imaging resolution of 4.2 μm in free space, corresponding to 3.1 μm in tissue, which is a six-fold improvement over prior art systems. For the first time, a SH-OCT system is applied to image the biological tissue of a native, intact rat-tail tendon. Highly contrasting, high-resolution SH-OCT images showing collagen fibrils organization in tendon tissue have been recorded.

In the invention, we demonstrate an optical tomography technique, second harmonic optical coherence tomography (SH-OCT), which combines the molecular contrast of SHG with the coherence gating of OCT. The SH-OCT system is comprised of an interferometer 20 illuminated by a broadband light source 12. If the sample 46 possesses certain structures lacking a center of symmetry, the illuminating light is converted into second harmonic waves at the sample site as well as in the reference arm 32 through a nonlinear crystal 34. The temporal interference pattern of these second harmonic waves is then detected and used for image construction. Because the fundamental radiation is only partially converted into second harmonics, with proper optics, both SH-OCT and conventional OCT measurements can be simultaneously performed. Based on the high selectivity of SHG on tissue molecular structure, together with optical sectioning capability of coherence gating, SH-OCT is provides considerable imaging contrast and resolution enhancement to the conventional optical tomographic imaging techniques.

The experimental configuration of SH-OCT system 10 is shown in FIG. 1a. The light source is a Kerr-lens mode-locked Ti:sapphire laser 12 with the output power of about 600 mW at a wavelength of 800 nm. The pulse duration is about 100-170 femtoseconds at a repetition rate of 76 MHz. The output of laser 12 is coupled through a Faraday isolator 16 to a half-wave plate 14 to prevent back-scattered light from entering laser 12 and interfering with mode locking. Half-wave plate 14 is used in combination with a Glan prism 18 and second half-wave plate 22 to control the input power into the optic fiber input into interferometer 20. A long-wave pass filter 24 is used to filter out the spurious second harmonic components produced by the laser 12.

Figure 5A:
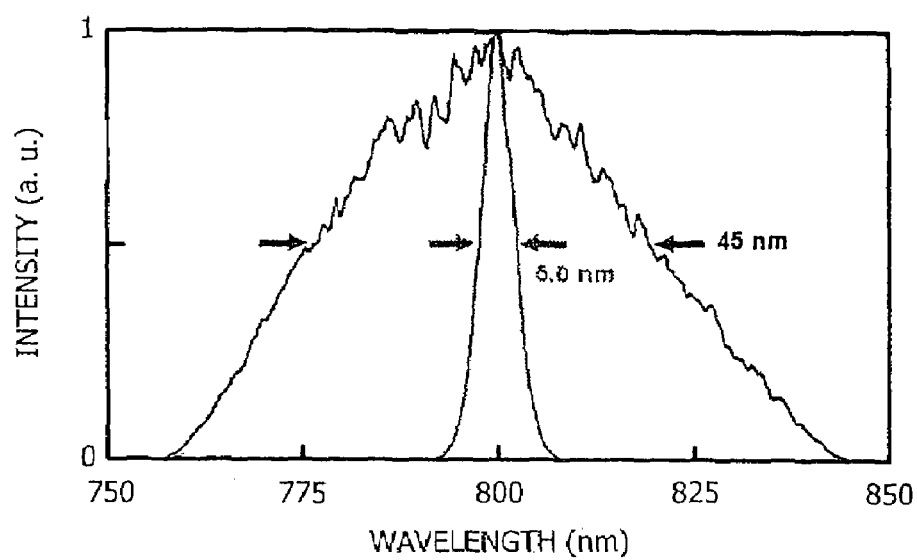
FIGS. 5a-5d show coherence length measurements in a high-resolution second harmonic OCT embodiment of FIG. 1b.

A fiber optic embodiment is depicted FIG. 1b and will be described together with the free-space embodiment of FIG. 1a. To generate a continuum centered at 800 nm, the femtosecond pulses from laser 12 are coupled through isolator 16, polarizer 23 and half wave plate 14 into a section of 2.0-meter-long commercially available high numerical aperture single mode fiber 17 (Corning HI-780) by a microscope objective 19 as shown in FIG. 1b. The invention also contemplates a free space optical path. When the optical path is provided in a fiber 17, the light output from the fiber 17 is re-collimated to a parallel beam with 1.5 mm diameter using an aspheric lens 21 in FIG. 1b. Glan laser polarizer 18 purifies the polarization of the continuum output. By rotating the half wave plate 14 in front of the coupling lens of the microscope objective in the high-resolution second harmonic OCT embodiment of FIG. 1b, a linear polarized continuum is produced in either horizontal or vertical polarization with an average power exceeding 200 mW. The spectrum broadening of the laser pulses in the fiber 17 is shown in FIG. 5a, where the narrow curve is the original spectrum of the laser 12 and the broadened curve is the spectrum of the continuum generated in the fiber. Note that the input beam polarization and the length of fiber 17 can affect the spectrum shape and smoothness.

Figure 1B:
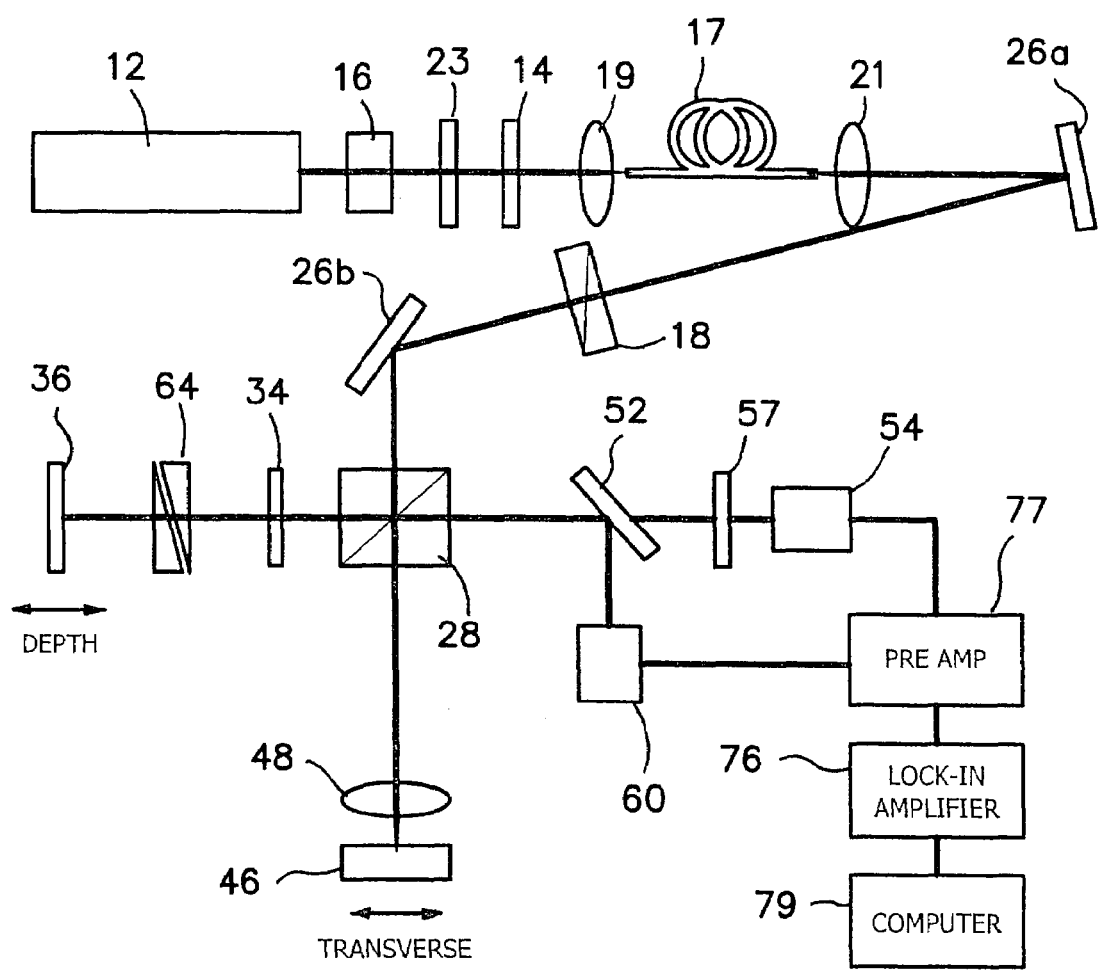
FIG. 1b is a schematic diagram of a second harmonic OCT apparatus with improved axial imaging resolution, which has a spectrum broadened pulsed light source using a single mode fiber optic and is implemented in a free-space Michelson interferometer configuration. This diagram is the high-resolution second harmonic OCT embodiment.

The filtered light is directed by mirrors 26a and 26b in FIG. 1b or mirror 26 in FIG. 1a into a polarizing beam splitter 28 which splits the input beam into the reference arm 32 and sample arm 30 of the interferometer 10. The split ratio is controlled by the second half-wave plate 22 upstream in the optical path.

In the reference arm 32, a 0.1 mm thick nonlinear $BaB_2O_4$ (BBO) crystal 34 is employed, which is oriented for type I phase matching, to convert the input radiation to second harmonic wave at 400 nm. Type I phase-matching means that both waves at the fundamental frequency ω have the same polarization whereas the wave at the second harmonic frequency 2ω have orthogonal polarization. Both second harmonic and fundamental waves are then reflected by a dichroic metal mirror 36 mounted on a motorized or piezoelectric translation stage 38, which acts as the delay line in OCT system 10. The back-reflected radiation is partially reflected by a broadband nonpolarizing beam splitter 40 and propagated into the combining broadband, nonpolarizing beam splitter 42. The dichroic mirror 36 reflects 90% of the second harmonic wave and 5% of the fundamental wave. A majority of the fundamental wave is dumped to avoid being reflected back to generate a second harmonic wave from the crystal 34 again, otherwise ghost lines may appear in the tomographic images.

In the signal arm after beam splitter 28 the fundamental radiation is transmitted through a half-wave plate 44 and is focused by a low numerical aperture lens 48 (N.A.=0.2, f=31.8 mm) onto sample 46 mounted on translation or scanning stage 50. When the sample 46 has second order nonlinear properties, the fundamental radiation generates a second harmonic signal. Back reflected second harmonic and fundamental waves were collimated by the same lens 48 and directed by a dichroic beam splitter 52 in the embodiment of FIG. 1a toward the combining beam splitter 42. The dichroic beam splitter 42 reflects a maximum amount of second harmonic radiation and about 5% of the fundamental radiation. In the embodiment of FIG. 1b the returned signal from sample 46 is directed to beam splitter 28 and then toward dichroic beam splitter 42 where it is split between a bandpass filter 57 and PMT 54 on one hand and photodiode 60 on the other. The outputs of PMT 54 and photodiode 60 are then coupled to a preamplier 77 which serves as a data acquisition and processing circuit and thence to lock-in amplifier 76 and computer 79.

In the embodiment of FIG. 1a the radiation from signal arm 30 and reference arm 32 are recombined after passing through the combining beam splitter 42. In the detection arm, a dichroic beam splitter 42 is used to separate the beam according to the wavelength. Fundamental and second harmonic interference fringes are detected by a photo diode 60 and a photomultiplier 54, respectively. A band-pass filter 58 centered at 400 nm with 40 nm bandwidth is attached to the photomultiplier head to further reject background noise. By changing the optical path delay in the reference arm 32, the pulses overlap temporally and interference fringes at fundamental and second harmonic wavelengths are generated.

The harmonic interference fringe signal is detected by a photomultiplier tube 54 after passing through a short-pass filter 56 which transmits light that is lower in wavelength than a predetermined value, which is chosen here to be below 800 nm but above 400 nm, and a 400 nm band-pass filter 58. The fundamental interference fringe signal is detected by a photodiode 60 after passing through a longpass filter 62 which transmits all the wavelengths longer than a predetermined wavelength number, which is set here below 800 nm but above 400 nm. A pair of prisms 64 made from BK7 glass are also inserted made from fused silica are inserted into the optical path of the signal arm 30 in the embodiment of FIG. 1a to compensate for the group-velocity dispersion of the fundamental and harmonic waves or group velocity mismatch in the two arms 30 and 32, thus enabling simultaneous observation of SH-OCT and conventional OCT signals. Because the material dispersion of the optical components is not uniform for all the wavelengths, the fundamental and second harmonic waves require different thicknesses of compensating material to generate optimized fringes at corresponding wavelengths. It is also within the scope of the invention that prism pair 64 could be inserted into the reference arm 32 between the crystal 34 and mirror 36 as shown in FIG. 1b.

To investigate the longitudinal resolutions for the fundamental and harmonic wavelengths in this hybrid OCT system 10, a polished GaAs (111) crystal is used in place of sample 46 as a nonlinear optical mirror 66 to have the interference fringes generated at both the harmonic and fundamental wavelengths. The experiment setup in FIG. 1a is modified by replacing the module 68 in the dotted box with module 70 in the dotted box. The laser 12 is focused at 45° onto the surface of crystal 66, and the reflected radiation (fundamental and second harmonic) is recollimated by another lens 48' identical to lens 48 and directed by mirrors 72 and 74 into beam splitter 42.

Interference signals of fundamental and second harmonic waves are measured as shown in the graph of FIG. 2, where second harmonic interference occurs at the double frequency of fundamental interference. The penetration depth of the 800 nm wavelength into the GaAs mirror 66 is less than one micron so the resolution of the system 10 is determined by the coherence length of laser radiation.

Figure 3A:
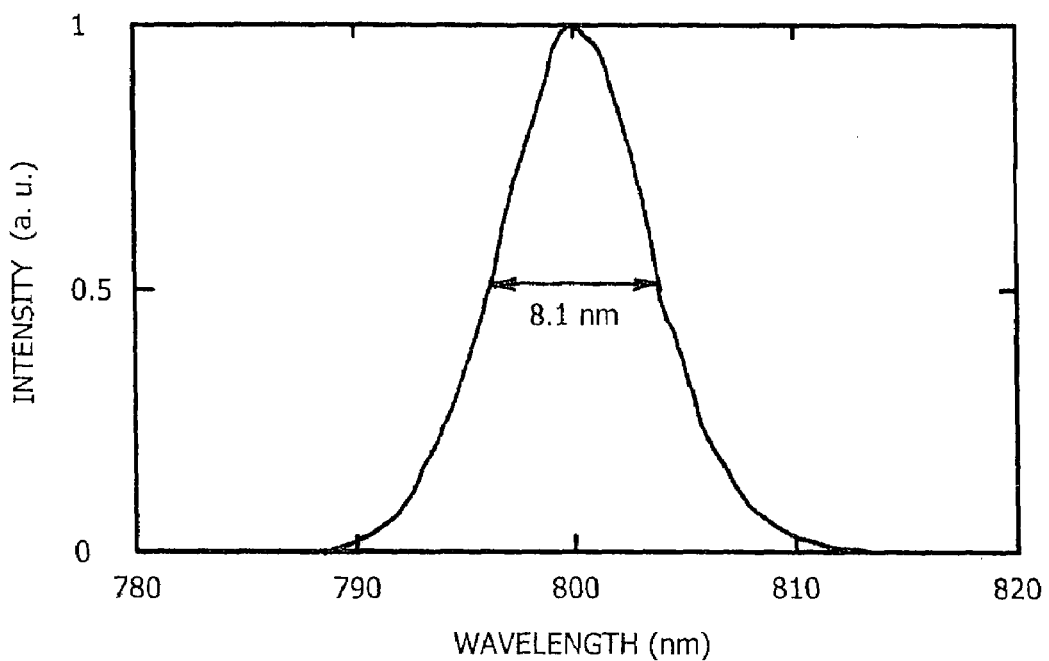
Figure 3B:
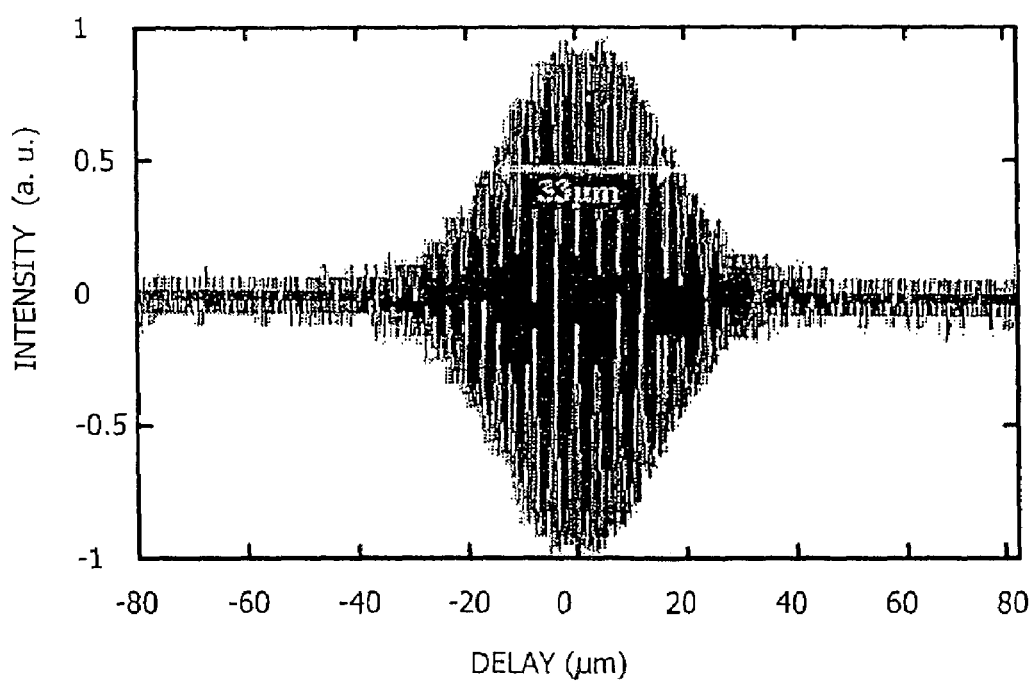
Figure 3C:
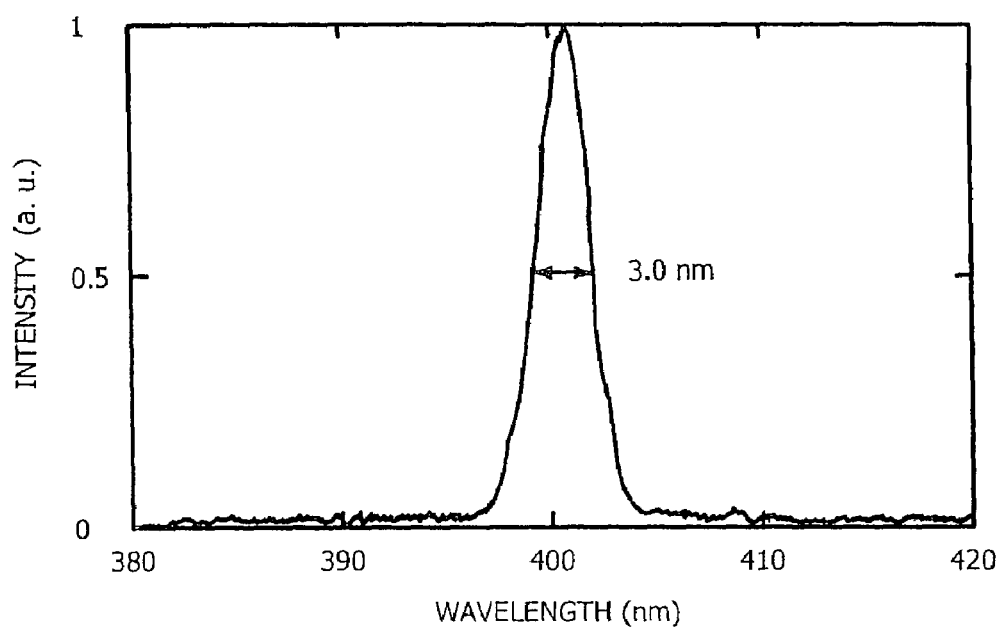
Figure 3D:
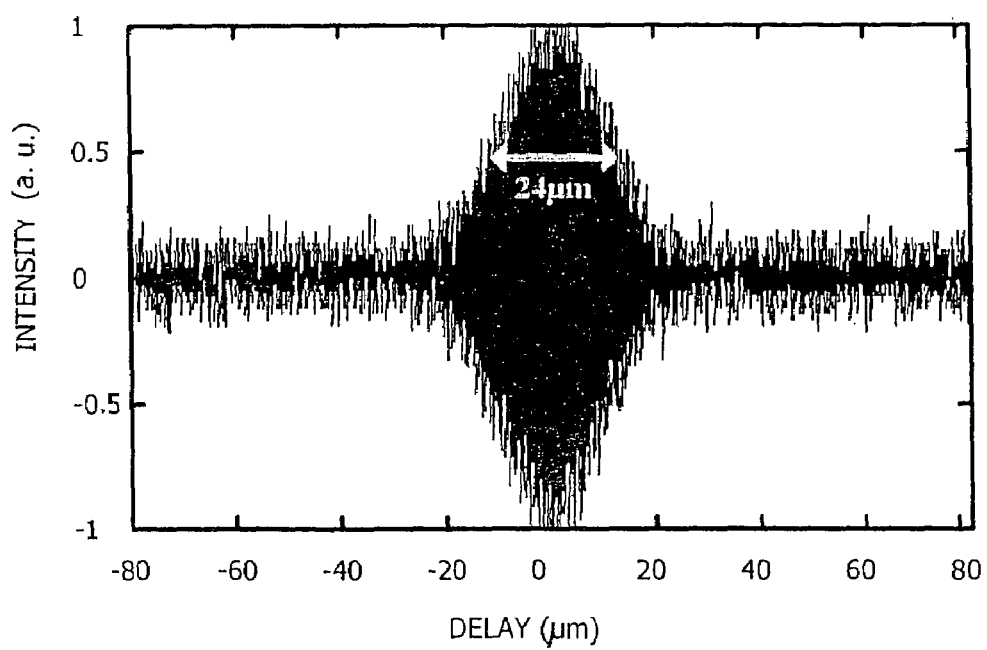

It is well known that the coherence length $l_c$ of a Gaussian pulse with spectral width $\Delta\lambda$ and center wavelength $\lambda_0$ is $l_c = 0.440 \lambda_0^2/\Delta\lambda$. Simple calculations show that for Gaussian pulses $\Delta\lambda_1/\Delta\lambda_2 = 4/\sqrt{2}$ and $l_c/l_{c2} = \sqrt{2}$, where $\Delta\lambda_1$ and $\Delta\lambda_2$ are the spectral width of fundamental and second harmonic waves, $l_c$ and $l_{c2}$ are the coherence lengths of the fundamental and second harmonic waves. The emission spectrum of the laser 12 in the illustrated embodiment is centered at 800 nm with a spectral width (full width at half-maximum) of 8.1 nm, as shown in FIG. 3a. The measured spectrum of SHG from the nonlinear crystal BBO 34 is shown in FIG. 3b, with a spectral width of 3.0 nm centered at 400 nm. FIG. 3c and FIG. 3d are graphs which represent the measured interference fringes of fundamental and harmonic waves when the mirror 36 is scanned. The measured coherence lengths of the fundamental and harmonic waves are 33 μm and 24 μm in free space respectively, which agree well with the predicted values within the experimental accuracy.

Figure 5B:
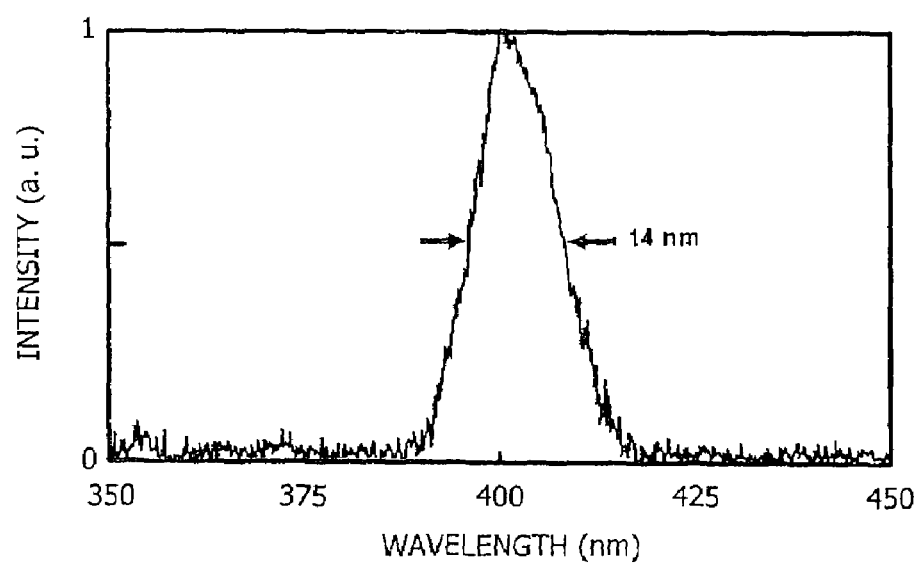
Figure 5C:
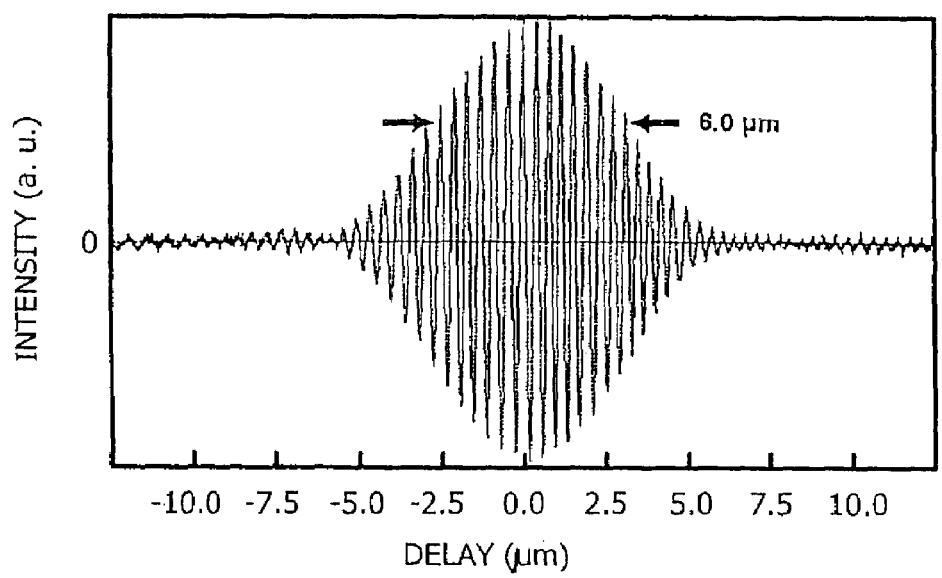
Figure 5D:
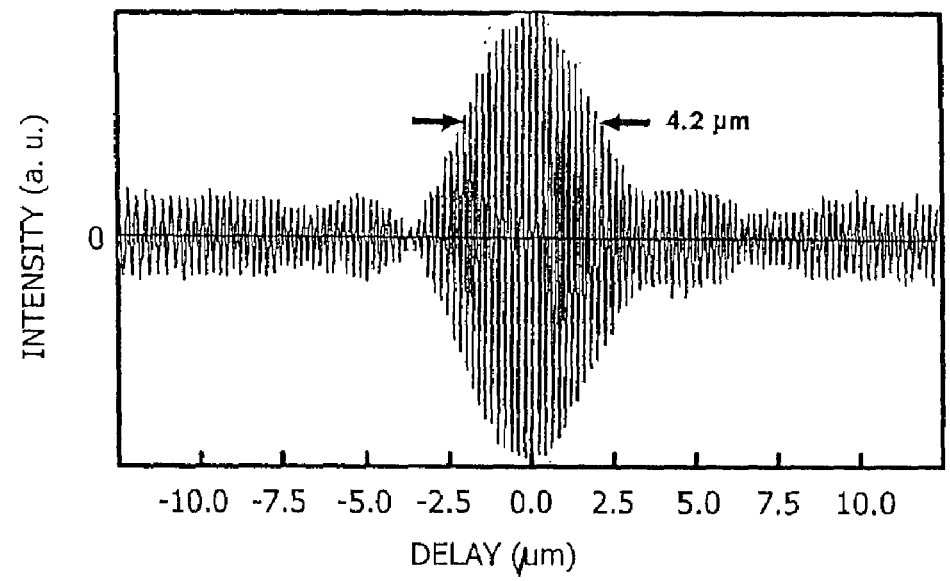

In the high-resolution second harmonic OCT embodiment of FIG. 1b, to measure the coherence length of the OCT system 10, we remove the BBO crystal 34 from the reference arm 32 and place crystal 34 in front of the main beam splitter 42, and replace the sample 46 with a mirror. Fundamental and second harmonic waves are present in both arms 30 and 32 and interfere to produce two sets of fringes, with the coherence point spread functions shown in FIG. 5c and FIG. 5d. The fundamental wave has a coherence length of 6.0 μm and the second harmonic wave has a coherence length of 4.2 μm in free space, which determine the axial resolutions of the OCT system at corresponding wavelengths. The spectrum of the second harmonic wave from the 0.1-mm-thick BBO crystal 34 is shown in FIG. 5b.

Figure 1C:
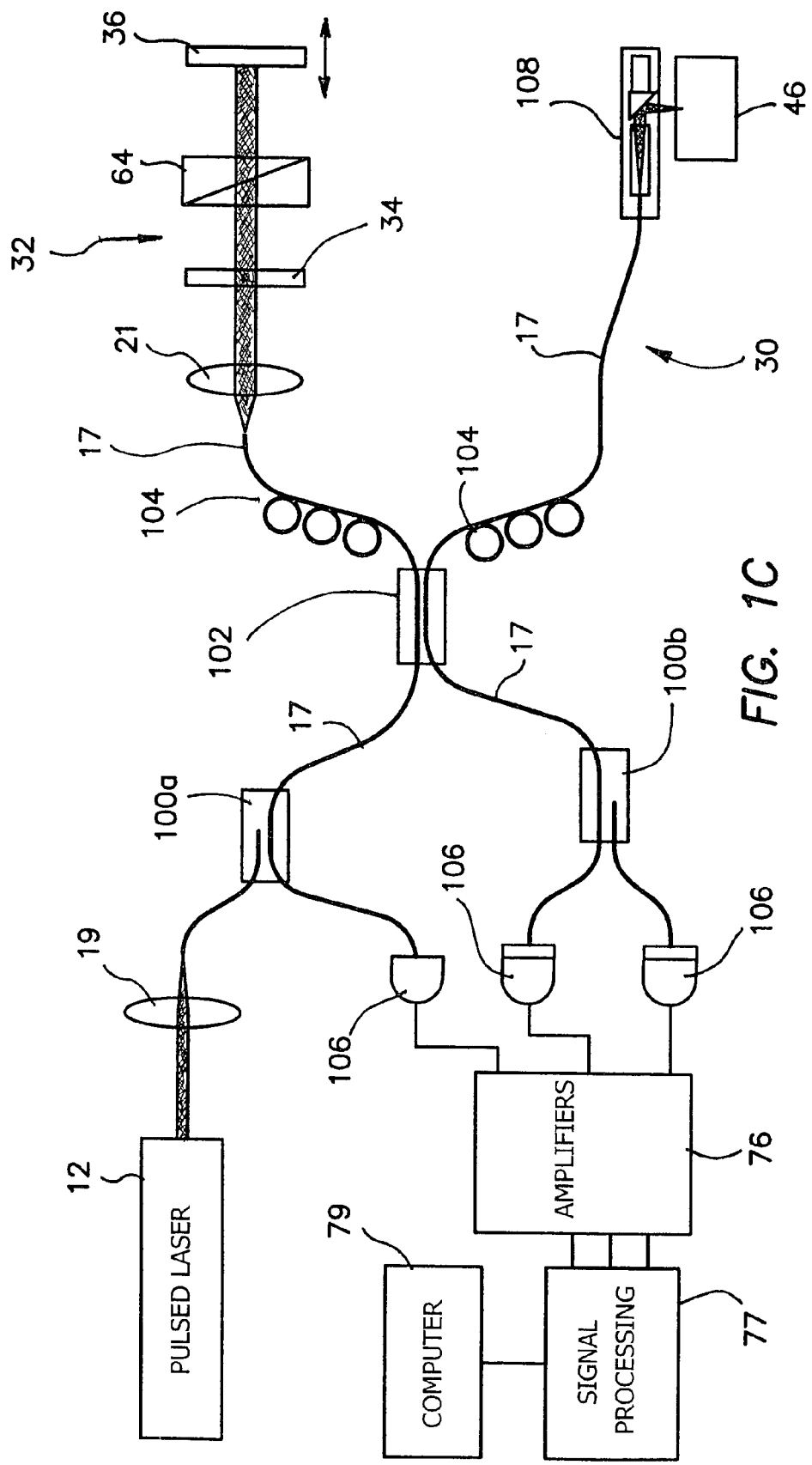
FIG. 1c is a schematic diagram of a second harmonic OCT apparatus implemented in a fiber-optic interferometer configuration. This diagram is the fiber-based second harmonic OCT embodiment.

In the fiber-based second harmonic OCT embodiment of FIG. 1c, the free-space optical paths of FIGS. 1a and 1b are replaced with optic fibers, and the free-space optical components are replaced with fiber-optic counterparts according to well understood design principles. For example, the free-space beamsplitters/combiners 28, 40, 42, 52 are replaced with 1×2 fiber-optic couplers 100 or 2×2 fiber-optic couplers 102, and the free-space polarization optics of laser polarizers and waveplates 14, 22, 23, 44, are replaced with fiber-optic polarization controllers 104, and the free-space optical detectors 54, 60 are replaced with fiber-interfaced detectors 106. Sample 46 is scanned using an fiber optic probe 108.

In the fiber-based second harmonic OCT embodiment of FIG. 1c, the 2×2 fiber-optic coupler 102 is for splitting and combining the light wave at second harmonic and fundamental frequency, one 1×2 fiber-optic coupler 100a is for monitoring the light intensity fluctuation in the light source 12, another 1×2 fiber-optic coupler 100b is for splitting the interference signals onto two detectors 106 for detecting the second harmonic frequency and fundamental frequency respectively. The fiber-optic polarization controllers 104 are for controlling and matching the polarization of light in both arms 30, 32 to produce maximum interference signals. The fiber-interfaced detectors 106 can be a fiber-interfaced photodiode, a avalanche photodiode or a photomultiplier tube.

In the fiber-based second harmonic OCT embodiment of FIG. 1c, the optical fiber 17 is chosen to support pulsed light propagation and support wideband single mode operation. Pulsed light propagation is required because in the nonlinear process of second harmonic generation, sufficient optical peak power can occur only when the pulses are present. Wideband single mode operation is required because it is desirable to collect the second harmonic signals from a pre-determined optical path and with high efficiency. Large mode area photonics crystal fibers and photonics band-gap fibers are two candidates to construct the fiber-based system.

Consider now the use of system 10 first to measure an actual biological sample 46. The sample 46 used in our study was Type I collagen harvested from rat tail tendon which is a well documented source of SHG in tissue. The sample consisted of two collagen layers 82 of about 30 µm thickness sandwiched among three 170 µm-thick glass slides 84, with its structure shown in FIG. 4c. The average excitation power entering the sample arm was approximately 50 mW.

Rat-tail tendon was chosen for the imaging experiment since many of its important properties are known from other independent methods. Collagen is the most abundant protein in higher vertebrates, comprising over one-third of total body protein and 60-86 percent or more of the dry weight of the tendon. Other components of tendons include water, proteoglycans, cells, elastin, and other extracellular matrix components. All of these components are arranged in a fibrous structure, as shown in a 60× microscope image in FIG. 6b. It is known that collagen in rat-tail tendon consists of three parallel intertwined, polar helices. This non-central-symmetric structure makes it very efficient for second harmonic generation.

Using Gaussian beam approximation, estimated power density at the beam waist in the sample was about $3.19 \times 10^9$ W/cm$^2$, and the focusing lens 48 had a depth of focus of 0.52 mm, which was long enough to cover the two collagen layers. In this case, back-reflected SHG signals from the sample 46 can be easily detected. The measured SHG signal was the contribution of the SHG signal reflected from a thin layer at the collagen layer surface and the transmitted SHG waves generated at various planes along the light path. The latter can be back scattered by the non-uniformities within the sample or at the boundaries of the different sample layers.

Figure 4A:
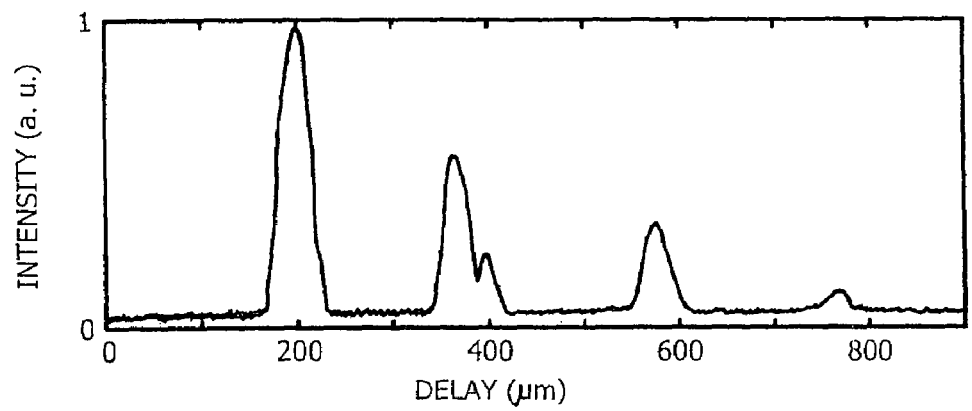
FIGS. 4a and 4b are conventional OCT and second harmonic OCT signals respectively of one axial scan of the phantom shown in FIG. 4c.
Figure 4B:
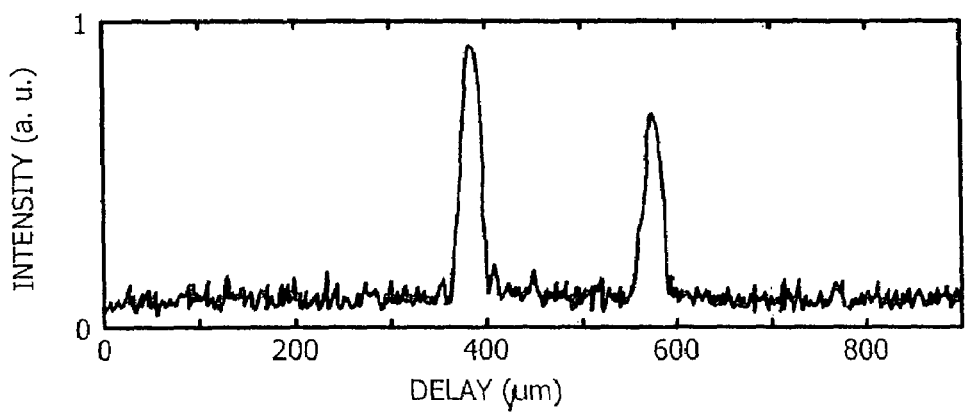
Figure 4C:
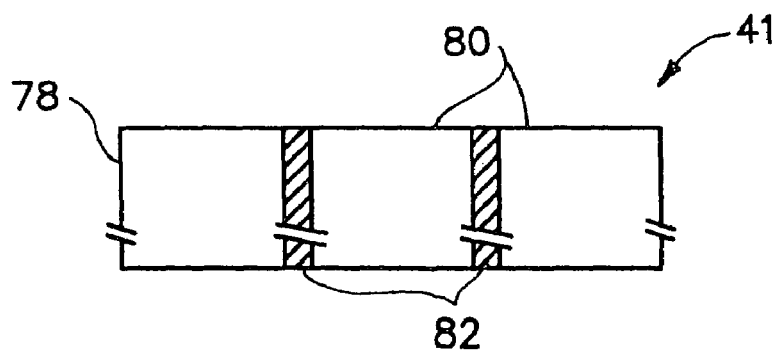

FIG. 4c is a side cross-sectional view of a phantom manufactured with three glass layers 80 sandwiching collagen layers 82. The tomography experiment was conducted by scanning the mirror 36 in the delay line of reference arm 32 and recording the fundamental and harmonic interference signals with a lock-in amplifier 76 coupled to PMT 54 and photodiode 60. The lock-in amplifier 76 demodulated the interference fringe envelope signal with extremely high sensitivity and precision when its frequency was locked at $f_{1,2} = 2v\, \Delta l / \lambda_{1,2}$, where v and $\Delta l$ are the frequency and amplitude respectively of the moving mirror 36, and $\lambda_{1,2}$ are the wavelengths of the fundamental and second harmonic waves. The output of amplifier 76 is coupled to an analog-to-digital converter 77 and thence to computer 79 where data reduction and storage is performed according to well understood principles to create the actual SH-OCT image.

The measured OCT signals of one typical axial scan are shown in the graph of FIG. 4a. The conventional OCT signal in FIG. 4a shows the sandwich structure of the sample 46 shown in FIG. 4c. The strong reflectance occurring at the first air-glass interface 78 suppresses signals from following layers. The SH-OCT signal in FIG. 4b shows two peaks that correspond to the two-layer structure as second harmonic signals are only produced in the two collagen layers 80 and 82. Comparison of FIG. 4a and FIG. 4b shows that there is no SH-OCT signal come from the air-glass interface 78, indicating that SH-OCT provides good contrast to linear reflections. The SH-OCT signal reveals information regarding the second-order nonlinear properties of the sample 46 that can not be provided by conventional OCT signals. Furthermore, it is evident that the resolution of SH-OCT is higher than that of conventional OCT.

In addition to molecular sensitivity, SHG also can serve as a unique contrasting mechanism for tissue structure since the second harmonic signal is highly dependent on the orientation, polarization, and local symmetry properties of tissue. Therefore, the SHG efficiency in collagen depends on orientation of collagen fibrils relative to the incident electric field polarizations. In the experiment of FIGS. 4a-4c, the half-wave plate 44 for the fundamental wavelength was used to control the input beam polarization to the sample 46. To maximize the second harmonic interference signal, another half-wave plate 84, shown in dotted outline and optimized for the second harmonic wavelength, is inserted into the reference arm 32 after the reference crystal 34. By rotating half-wave plates 44 and 84 in both arms 30 and 32, collagen fibrils with different orientation can be preferentially highlighted to produce polarization dependent tomographic images.

In another measurement of rat tail tendon the images of FIGS. 6a and 6b were obtained. In this study, rat-tail tendon was removed from thawed rat-tails and stored in phosphate-buffered saline solution for several minutes. A 10-mm-long section was cut from the tendon and embedded between two microscope cover slips spaced by 0.1 mm diameter wire ring. The edge of the sample was sealed with epoxy.

We used a microscope objective to focus the beam onto the specimen. The average laser power was 80 mW at the sample site. Typical energy per pulse was approximately 1 nJ with energy density of 0.05-0.07 J/cm$^2$, which is much less than the tissue damage threshold in the range of 0.5-1.0 J/cm$^2$. When the optical path length difference between the sample arm 30 and reference arm 32 is within the coherence length of the second harmonic wave, the second harmonic interference can be detected. The interference fringes signal was demodulated by lock-in amplifier 76 and used for image construction. FIG. 6a shows a high-resolution SH-OCT image in the rat-tail tendon obtained with a 0.25-µm scanning resolution. The image shows the collagen fibrils organization within an area of 100×50 µm. As the tension-bearing element in the tendon, collagen appears in clearly defined, parallel, cable-like and slightly wavy bundles. In this image, highly organized collagen fiber bundles (fascicles) oriented in the same direction can be clearly identified. Because of the cross-sectioning nature of OCT, collagen fiber bundles localized at different imaging planes parallel to the axial direction exhibit different thicknesses as projected into this image. The transverse and axial resolutions of this image are 1.9 μm and 4.2 μm, as determined by the Gaussian beam waist diameter at the focus and coherence length of second harmonic wave respectively.

Understanding the origin of the back-scattered SHG signal from the sample is important because in the coherent process of SHG, the majority of the second-harmonic wave co-propagates with the excitation laser beam. This phenomenon has been experimentally investigated in nearly transparent thin layers. The research results suggest that laterally oriented collagen fibrils scatter in both forward and backward directions, but axially oriented collagen fibrils scatter mostly forward with signal intensity orders of magnitude larger than lateral ones. In highly scattering thick tissues like tendons and muscles, essentially no SHG signals can be collected in transmission mode, and the SHG signals detected in the backward direction are mostly from the back scattering of the forward-generated SHG signals, since SHG signals are predominantly generated in forward direction, and immediately suffer from heavy scattering within the tissue until they either get absorbed or escape from the sample surface in the backward direction. Collected by the same excitation objective, these back-scattered SHG signals are particularly important for thick tissues and in-vivo clinical applications.

Figure 7A:
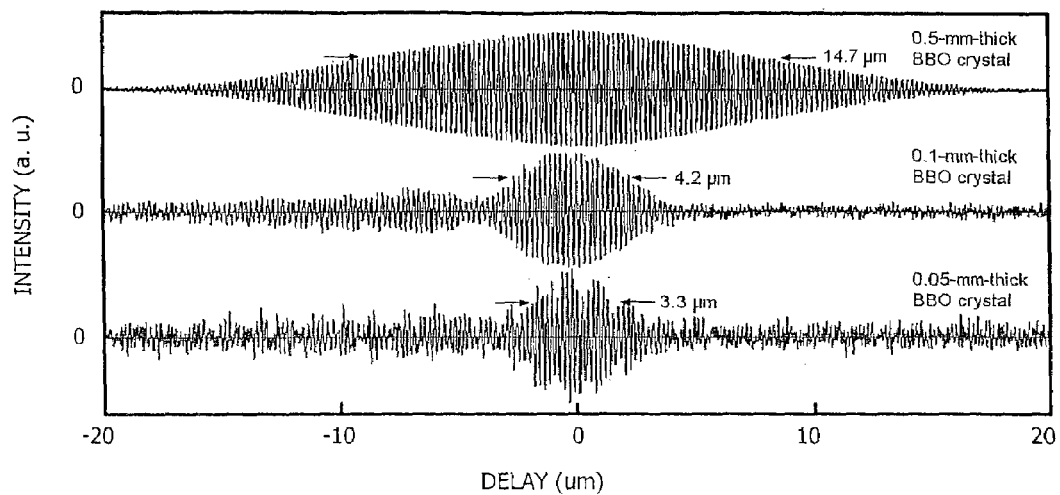
FIG. 7a shows graphs of self-normalized SHG interference fringes from BBO crystals of 0.5, 0.1 and 0.05 mm thicknesses. The measured coherence lengths are also shown in the figure.
Figure 7B:
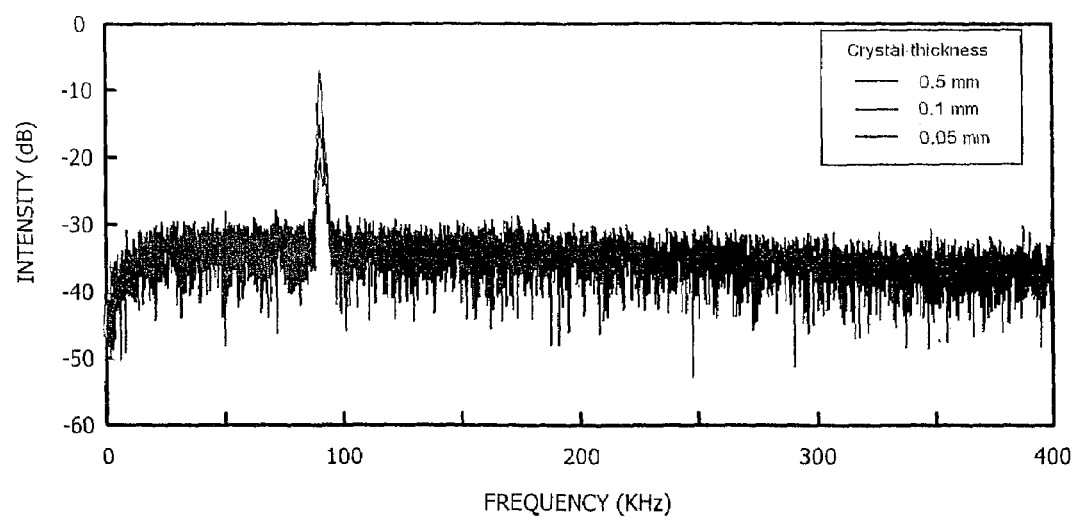
FIG. 7b is a graph of the Fourier transforms of the SHG interference fringes for the same three different crystal thickness and are shown to be inseparably overlapped.

The BBO crystal 34 used in the reference arm has a thickness of 0.1 mm and is oriented for type-I phase matching. For second harmonic wavelength conversion of a broadband laser source 12 using a nonlinear crystal, spectrum narrowing effect induced by the crystal dispersion must be considered. Because the spectral width of SHG in the bulk of a nonlinear crystal is limited by the crystal thickness, the nonlinear crystal has to be made very thin to accommodate for a large bandwidth of the fundamental laser spectrum. Under the same excitation conditions, the coherence lengths measured when using different thickness crystals are shown in FIG. 7a, and the Fourier transforms of the measured fringes are shown in FIG. 7b. Although thicker crystal (0.5 mm) produces much greater SHG signals than thinner ones (0.1 and 0.05 mm), its coherence length is also much larger, which means thicker crystal limits the SHG spectrum more than thinner crystal. However, further reducing crystal thickness from 0.1 mm to 0.05 mm does not generate much more useful spectral components, but produces even weaker SHG signals. Therefore, a 0.1 mm is an optimum crystal thickness for balanced SHG signal strength and spectral width in current system.

The BBO crystal 34 can also work as the polarization selector for the second harmonic interference. With current experiment setup in FIG. 1a, when the crystal 34 is followed by another quarter wave plate designed for the second harmonic wavelength, the polarization plane of second harmonic wave in the reference arm can be rotated to match that from the sample to produce polarization selective SH-OCT images.

Collagen is the predominant structural protein in most biological tissues, as well as the major source of SHG. Modifications of the collagen fibrillar matrix structure are associated with various physiologic processes, such as wound healing, aging, diabetes, and cancer. Research results suggest morphologic changes in collagen structure produces predictable alterations in the SHG signal, and can be intrinsic indicators of disease states. Therefore, SHG is very promising as a sensitive probe in tissue morphology and physiology studies. With the development of novel microstructure fibers that support femtosecond laser pulses, it is possible to implement SH-OCT with fiber optics and adapt it for in-vivo endoscopic imaging inside bodies of living animals and human patients.

In summary, we have presented a noninvasive optical tomography technique of second harmonic optical coherence tomography and experimentally demonstrated the feasibility of using this technique to image biological samples. Compared with conventional OCT performed at fundamental wavelength, SH-OCT offers enhanced molecular contrast and spatial resolution. It is also an improvement over existing second harmonic scanning microscopy technology as the intrinsic coherence gating mechanism enables the detection and discrimination of second harmonic signals generated at deeper locations. The enhanced molecular contrast of SH-OCT extends conventional OCT's capability for detecting small changes in molecular structure. Second harmonic-OCT is promising for the diagnosis of cancers and other diseases at an early stage when changes in tissue and molecular structure are small.

Detailed structural information about collagen fibrils organization in rat-tail tendon has been revealed in the recorded images. This new technique may offer several distinct advantages for imaging ordered, or partially ordered, biological tissues. First, the SHG signal from tissue tends to be a very sensitive indicator of tissue molecular structure and symmetry changes. Second, coherence gating extends the capability of high-resolution detection of SHG signals at locations deep inside the sample. Third, SHG signals are produced intrinsically so imaging does not require staining the sample with dyes or fluorophores. Fourth, decoupled axial and transverse scans enable two dimensional tomographic imaging of sample with only one dimension moving of the probing beam, which is essential for in-vivo endoscopic applications.

Many alterations and modifications may be made by those having ordinary skill in the art without departing from the spirit and scope of the invention.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for second harmonic optical coherence tomography of a sample comprising:
   a light source;
   an interferometer having an optical path in a reference arm and in a sample arm;
   a nonlinear crystal in the optical path of the reference arm, the sample having at least some second harmonic backscattering of light from the light source and being in the optical path of the sample arm;
   a broadband beam splitter optically coupled to the reference arm and sample arm, combines the signals in the reference arm and sample arm into interference fringes;
   a dichroic beam splitter optically coupled to the broadband beam splitter to split the interference fringes into a fundamental and second harmonic interference signal; and
   a detector optically coupled to the dichroic beam splitter for detecting interference fringes.

2. The apparatus of claim 1 where the detector detects second harmonic interference fringes.

3. The apparatus of claim 1 where the detector comprises two separate detectors, one of which detects fundamental and the other one of which detects second harmonic interference fringes.

4. The apparatus of claim 1 further comprising a pair of prisms in the optical path of the signal arm or reference arm to compensate for the group-velocity dispersion of the fundamental and harmonic waves or group velocity mismatch in the signal arm and reference arm, thus enabling simultaneous observation of SH-OCT interference signals and conventional OCT interference signals.

5. The apparatus of claim 1 where the interferometer comprises means for independently axially or transversely scanning the sample in decoupled modes of operation to provide two dimensional tomographic imaging of the sample with only one dimensional movement of the light.

6. The apparatus of claim 1 where the light source comprises a femtosecond pulsed laser.

7. The apparatus of claim 1 where the interferometer and detector simultaneously perform second harmonic OCT measurements at a second harmonic frequency and OCT measurements at a fundamental frequency.

8. The apparatus of claim 1 further comprising means for controlling input power into the interferometer.

9. The apparatus of claim 1 where the light source comprises a mode-locked laser and further comprising means for preventing back-scattered light from entering the light source and interfering with mode locking.

10. The apparatus of claim 1 further comprising means for filtering out second harmonic frequencies of light generated by the light source and transmitted from the light source toward the interferometer.

11. The apparatus of claim 1 further comprising means optically coupled to the light source for determining a ratio of polarization modes of the light generated by the light source and transmitted toward the interferometer and further comprising means for splitting the light from the light source into the reference arm and sample arm according to polarization mode of the light, the means for splitting being optically coupled to the means for determining a ratio of polarization modes.

12. The apparatus of claim 1 where the nonlinear crystal is oriented for type I phase matching.

13. The apparatus of claim 1 further comprising a dichroic mirror and translation stage coupled to the mirror to provide an optical terminus in the reference arm to act as an optical delay line.

14. The apparatus of claim 13 where the dichroic mirror differentially reflects the fundamental and second harmonic frequency of the light signal in the reference arm to reduce the amount of reflected light at the fundamental frequency, which is transmitted toward the nonlinear crystal.

15. The apparatus of claim 1 further comprising a bandpass filter centered at the second harmonic frequency and optically coupled to the dichroic beam splitter for rejecting background noise transmitted toward the detector.

16. The apparatus of claim 3 further comprising a long pass filter and short pass filter to differentiate between the fundamental and second harmonic frequency interference signals, where the detector which detects the fundamental frequency is optically filtered by the long pass filter and where the detector which detects the second harmonic frequency is optically filtered by the short pass filter.

17. The apparatus of claim 1 further comprising a moving mirror in the reference arm and a lock-in amplifier coupled to the detector, where the lock-in amplifier is locked at $f_{1,2}=2v\,\Delta l\,/\lambda_{1,2}$, where v and $\Delta l$ are the frequency and amplitude respectively of the moving mirror, and $\lambda_{1,2}$ are the wavelengths of the fundamental and second harmonic interference signals.

18. The apparatus of claim 1 further comprising means for controlling the beam polarization of light in the sample arm and reference arm, oriented according to polarization characteristics of the sample.

19. The apparatus of claim 1 where the nonlinear crystal has a predetermined thickness according to the wavelength of the fundamental frequency for balanced SHG signal strength and spectral width.

20. The apparatus of claim 1 where the nonlinear crystal has a predetermined thickness of approximately 0.1 mm when the wavelength of the fundamental frequency is approximately 800 nm.

21. A method of performing optical tomography of a sample comprising:
   providing a source of at least partially coherent broadband radiation through an interferometer having a sample arm for probing the sample and a reference arm;
   scanning the sample with the source of radiation through the interferometer;
   generating first and second harmonics from the sample and from a nonlinear thin crystal in the reference arm;

detecting interference fringes of the first and second harmonics radiation backscattered from the sample into the interferometer;

processing the detected interference fringes to determine first and second harmonics OCT signals of the detected backscattered interference fringes at each pixel in a data window; and generating a tomographic image of the sample based on the first and second harmonics OCT interference fringes at different spatial locations in the sample disDlayed as different pixels in a final image.

22. An apparatus for performing optical tomography of a sample in which second harmonics of a radiation signal can be generated comprising:

a source of at least partially coherent broadband radiation;

an interferometer coupled to the source having and a reference arm and a sample arm for probing the sample;

a scanner for scanning the sample with radiation from the source provided through the interferometer;

a nonlinear thin crystal in the reference arm for generating second harmonics;

a detector for detecting interference fringes of the first and second harmonics of the radiation backscattered from the sample into the interferometer; and a processor coupled to the detector to determine first and second harmonic OCT signals of the detected backscattered interference fringes different optical delays between the sample and reference arms, and to simultaneously generate a tomographic image of the sample based on the first and second harmonics OCT interference fringes at different spatial locations in the sample displayed as different pixels in a final image.

23. An improvement in an OCT tomographic imaging system having an interferometer with a reference arm and sample arm comprising:

means for generating a second harmonic frequency in the reference arm;

means for combining the second harmonic frequency from the reference arm and a second harmonic frequency from the sample in the sample arm to produce a second harmonic interference fringe signal; and means for detecting the second harmonic interference fringe signal to enable the OCT tomographic imaging system to produce an image derived from the second harmonic interference fringes at different spatial locations in the sample displayed as different pixels in a final image.

24. A method for second harmonic optical coherence tomography of a sample comprising:

generating light at a fundamental frequency;

coupling the light at a fundamental frequency into an interferometer having an optical path in a reference arm and in a sample arm;

generating a second harmonic of the light in the optical path of the reference arm;

generating a second harmonic of the light in the optical path of the sample arm depending on the nonlinear optical properties and optical scattering characteristics of the sample;

combining the second harmonic of the light from the reference arm and the sample arm to generate a second harmonic interference fringes at different spatial locations in the sample displayed as different pixels in a final image; and detecting the second harmonic interference fringe signal based on scattering from the sample.

25. The method of claim 24 where generating a second harmonic of the light in the optical path of the reference arm comprises generating the second harmonic of the light by means of a nonlinear crystal.

26. The method of claim 24 where combining the second harmonic of the light from the reference arm and the sample arm to generate a second harmonic interference fringe signal comprises combining the second harmonic of the light from the reference arm and the sample arm in a dichroic beam splitter, which splits the interference fringes into a fundamental and the second harmonic interference signal.

27. The method of claim 26 further comprising simultaneously detecting the fundamental harmonic interference fringe.

28. The method of claim 24 further comprising compensating for the group-velocity dispersion of the fundamental and harmonic waves or group velocity mismatch in the signal arm and reference arm, thus enabling simultaneous observation of SH-OCT interference signals and conventional OCT interference signals.

29. The method of claim 24 further comprising independently axially scanning in with optical delay in the reference arm and transversely scanning the sample with the beam from the sample arm in decoupled modes of operation to provide two dimensional tomographic imaging of the sample with only one dimensional movement of the light.

30. The method of claim 24 where generating light at a fundamental frequency comprises generating femtosecond light pulses from an least partially coherent light source.

31. The method of claim 24 further comprising performing OCT measurements at a fundamental frequency simultaneously with performing OCT measurements at a second harmonic frequency.

32. The method of claim 24 further comprising controlling input power into the interferometer.

33. The method of claim 24 where generating light at a fundamental frequency comprises generating light in a mode-locked laser and preventing back-scattered light from entering the laser and interfering with mode locking.

34. The method of claim 24 further comprising filtering out second harmonic frequencies of light transmitted into the interferometer.

35. The method of claim 24 further comprising generating a ratio of polarization modes of the light transmitted into the interferometer and splitting the light from the light source into the reference arm and sample arm according to polarization mode of the light.

36. The method of claim 24 where generating a second harmonic of the light in the optical path of the reference arm comprises generating the second harmonic of the light in a nonlinear crystal oriented for type I phase matching.

37. The method of claim 24 further comprising optically delaying the light in the reference arm using a dichroic mirror and translation stage holding dichroic mirror.

38. The method of claim 37 where optically delaying the light in the reference arm using a dichroic mirror and translation stage holding the dichroic mirror comprises differentially reflecting the fundamental harmonic from the second harmonic frequency of the light signal in the reference arm to reduce the amount of reflected light at the fundamental frequency in the reference arm to reduce or avoid generating a copy of the second harmonic signals in the reference arm which leads to ghost effects in a final image.

39. The method of claim 24 further comprising a bandpass filtering the interference fringe signal centered at the second harmonic frequency to reject background noise.

40. The method of claim 27 further comprising a long pass filtering and short pass filtering the interference fringe signal to differentiate between the fundamental and second harmonic frequency interference signals during detection.

41. The method of claim 24 further comprising moving a mirror in the reference arm and amplifying the detected interference fringe signal by means of a lock-in amplifier.

42. The method of claim 24 further comprising controlling the beam polarization of light in the sample arm and reference arm, oriented according to polarization characteristics of the sample.

43. The method of claim 24 where generating the second harmonic of the light in the optical path of the reference arm is by means of a nonlinear crystal which has a predetermined thickness selected according to the wavelength of the fundamental frequency for balanced SHG signal strength and spectral width.

44. The method of claim 24 where generating the second harmonic of the light in the optical path of the reference arm is by means of a nonlinear crystal which has a predetermined thickness of approximately 0.1 mm when the wavelength of the fundamental frequency is approximately 800 nm for balanced SHG signal strength and spectral width.

45. An improvement in a method of OCT tomographic imaging using an interferometer with a reference arm and sample arm comprising:
generating a second harmonic frequency in the reference arm;
combining the second harmonic frequency from the reference arm and a second harmonic frequency from the sample in the sample arm to produce a second harmonic interference fringe signal; and
detecting the second harmonic interference fringe signal to enable the OCT tomographic imaging system to produce an image derived from the second harmonic interference fringes at different spatial locations in the sample displayed as different pixels in a final image.

46. A method for performing optical tomography of a sample in which second harmonics of a radiation signal comprising:
generating at least partially coherent broadband radiation;
coupling the radiation to an interferometer having and a reference arm and a sample arm for probing the sample;
scanning the sample with radiation provided through the interferometer;
generating second harmonics in the reference arm;
detecting interference fringes of the first and second harmonics of the radiation backscattered from the sample into the interferometer;
detecting first and second harmonic OCT signals of the detected backscattered interference fringes at each pixel in a data window; and
simultaneously generating a tomographic image of the sample based on the first and second harmonics OCT interference fringes at different spatial locations in the sample displayed as different pixels in a final image.

47. An apparatus for performing optical tomography of a sample in which second harmonics of a radiation signal can be generated comprising:
a source of at least partially coherent broadband radiation;
a fiber-based interferometer coupled to the source having a reference arm and a sample arm for probing the sample;
a scanner for scanning the sample with radiation from the source provided through the interferometer;
a nonlinear thin crystal in the reference arm for generating second harmonics;
a detector for detecting interference fringes of the first and second harmonics of the radiation backscattered from the sample into the interferometer; and
a processor coupled to the detector to determine first and second harmonic OCT signals of the detected backscattered interference fringes at each pixel in a data window, and to simultaneously generate a tomographic image of the sample at each pixel based on the first and second harmonics OCT interference fringes.

48. The apparatus of claim 47 where the fiber-based interferometer comprises:
a 2×2 fiber-optic coupler for splitting and combining the light wave at second harmonic and fundamental frequency;
a first 1×2 fiber-optic coupler for monitoring the light intensity fluctuation in the light source;
a second 1×2 fiber-optic coupler for splitting the interference signals onto two detectors for detecting the second harmonic frequency and fundamental frequency respectively; and
two fiber-optic polarization controllers, one of the two fiber-optic polarization controllers being in the optical path in the reference and in the sample arm for controlling and matching the polarization of light in the corresponding reference and in the sample arm to produce maximum interference signals, and
where the detector comprises a fiber-interfaced detector.

49. The apparatus of claim 47 where the fiber-based interferometer has an optical path which comprises optical fibers chosen to support pulsed light propagation and support wideband single mode operation.

50. The apparatus of claim 49 where the optical fibers are large mode area photonics crystal fibers or photonics bandgap fibers.

51. An improvement in an OCT tomographic imaging system using an interferometer with a reference arm and sample arm to image a sample comprising:
a nonlinear crystal for generating third harmonic frequency in the reference arm;
means for combining the third harmonic frequency from the nonlinear crystal in the reference arm and any third harmonic frequency returned from the sample in the sample arm to produce a third harmonic interference fringe signal; and
means for detecting the third harmonic interference fringe signal to enable the OCT tomographic imaging system to produce an image derived from the third harmonic interference fringe signal.

52. An improvement in an OCT tomographic imaging system using an interferometer with a reference arm and sample arm to image a sample comprising:
a coherent Raman reference for generating a coherent Raman frequency in the reference arm;
means for combining the coherent Raman frequency from the coherent Raman reference in the reference arm and any Raman frequency from the sample in the sample arm to produce a coherent Raman interference fringe signal; and
means for detecting the coherent Raman interference fringe signal to enable the OCT tomographic imaging system to produce an image derived from the coherent Raman interference fringe signal.

* * * * *